United States Patent
Langley et al.

(10) Patent No.: US 10,405,818 B2
(45) Date of Patent: Sep. 10, 2019

(54) ANTIMICROBIAL HOUSING FOR DIGITAL DETECTOR

(71) Applicant: CARESTREAM HEALTH, INC., Rochester, NY (US)

(72) Inventors: Robert J. Langley, Pittsford, NY (US); Scott T. MacLaughlin, Pittsford, NY (US)

(73) Assignee: Carestream Health, Inc., Rochester, NY (US)

(*) Notice: Subject to any disclaimer, the term of this patent is extended or adjusted under 35 U.S.C. 154(b) by 199 days.

(21) Appl. No.: 15/492,036

(22) Filed: Apr. 20, 2017

(65) Prior Publication Data
US 2017/0303880 A1    Oct. 26, 2017

Related U.S. Application Data

(60) Provisional application No. 62/325,486, filed on Apr. 21, 2016.

(51) Int. Cl.
  *A61B 6/10* (2006.01)
  *A61B 6/00* (2006.01)
  *A61L 2/08* (2006.01)

(52) U.S. Cl.
  CPC .......... *A61B 6/4423* (2013.01); *A61B 6/4283* (2013.01); *A61B 6/4405* (2013.01); *A61L 2/088* (2013.01)

(58) Field of Classification Search
  CPC ... A61B 6/4283; A61B 6/4405; A61B 6/4423; A61L 2/088
  See application file for complete search history.

(56) References Cited

U.S. PATENT DOCUMENTS

| | | | |
|---|---|---|---|
| 5,383,934 A | 1/1995 | Armini et al. | |
| 7,041,723 B2 | 5/2006 | Kimura | |
| 8,623,446 B2 | 1/2014 | McGrath et al. | |
| 9,016,221 B2 | 4/2015 | Brennan et al. | |
| 9,125,973 B2 | 9/2015 | Bui et al. | |
| 9,354,326 B2 | 5/2016 | MacLaughlin et al. | |
| 2001/0047195 A1 | 11/2001 | Crossley | |
| 2002/0177767 A1 | 11/2002 | Burton et al. | |
| 2006/0029808 A1 | 2/2006 | Zhai et al. | |
| 2006/0188389 A1 | 8/2006 | Levy | |
| 2008/0149852 A1 | 6/2008 | Shoji et al. | |
| 2010/0193672 A1 | 8/2010 | Blasenheim et al. | |
| 2014/0037070 A1* | 2/2014 | Noguchi | A61B 6/4423 378/189 |

OTHER PUBLICATIONS

Shravanthi T. Reddy et al., "Micropatterned Surfaces for Reducing the Risk of Catheter-Associated Urinary Tract Infection: An In Vitro Study on the Effect of Sharklet Micropatterned Surfaces to Inhibit Bacterial Colonization and Migration of Uropathogenic *Escherichia coli*," Journal of Endourology, vol. 25, No. 9, Sep. 2011, pp. 1547-1552.

(Continued)

*Primary Examiner* — Mark R Gaworecki

(57) ABSTRACT

A digital radiography detector has a two dimensional array of photosensors, with control electronics electrically connected to the photosensors. A substantially rigid housing encloses the photosensors and the control electronics. A surface of the housing includes antimicrobial material to inhibit growth of pathogens.

16 Claims, 4 Drawing Sheets

(56) References Cited

OTHER PUBLICATIONS

Sagheer A. Onaizi et al., "Tethering antimicrobial peptides: Current status and potential challenges," Biotechnology Advances, 29, 2011, pp. 67-74.

Roya Dastjerdi et al., "A review on the application of inorganic nano-structured materials in the modification of textiles: Focus on anti-microbial properties," Colloids and Surfaces B: Biointerfaces, 79, 2010, pp. 5-18.

Akira Fujishima et al., "Titanium dioxide photocatalysis," Journal of Photchemistry and Photobiology C: Photochemistry Reviews 1, 2000, pp. 1-21.

S.Y. Liau et al., "Interaction of silver nitrate with readily identifiable groups: relationship to the antibacterial action of silver ions," Letters in Applied Microbiology, 1997, 25, pp. 279-283.

Philip J. Snodgrass et al., "Effects of Silver and Mercurials on Yeast Alcohol Dehydrogenase," The Journal of Biological Chemistry, vol. 235, No. 2, Feb. 1960, pp. 504-508.

Hiroyuki Yamada et al., "Direct Observation and Analysis of Bacterial Growth on an Antimicrobial Surface," Applied and Environmental Microbiology, Aug. 2010, pp. 5409-5414.

A.J. Isquith et al., Surface-Bonded Antimicrobial Activity of an Organosilicon Quaternary Ammonium Chloride, Applied Microbiology, Dec. 1972, pp. 859-863.

Christopher J. Ioannou et al., "Action of Disinfectant Quaternary Ammonium Compounds against *Staphylococcus aureus*," Antimicrobial Agents and Chemotherapy, Jan. 2007, pp. 296-306.

Sacha Noimark et al.,"Scientists Develop World's First Light-Activated Antimicrobial Surface That Also Works in the Dark," www.meddeviceonline.com/doc/scientists-light-activated-antimicrobial-surface-works-dark-0001, Mar. 24, 2014, printed Apr. 18, 2017, 3 pages.

A.D. Russell et al., "7 Antimicrobial Activity and Action of Silver," Progress in Medicinal Chemistry, vol. 31, 1994, pp. 351-370.

* cited by examiner

US 10,405,818 B2

ANTIMICROBIAL HOUSING FOR DIGITAL DETECTOR

CROSS REFERENCE TO RELATED APPLICATIONS

This application claims priority to U.S. Patent Application Ser. No. 62/325,486, filed Apr. 21, 2016, in the name of Robert J. Langley, and entitled ANTIMICROBIAL HOUSING FOR DIGITAL DETECTOR.

FIELD OF THE INVENTION

The invention relates generally to the field of medical imaging and more particularly relates to apparatus and methods for providing a portable wireless digital detector having a housing that is highly resistant to microbial activity and growth.

BACKGROUND

With the advent of portable wireless digital radiography (DR) detectors, hospitals and other healthcare facilities now have expanded capability for obtaining x-ray images, including images obtained at the patient bedside. Unlike conventional radiographic image detectors that can be mounted in fixed positions within an imaging system, wireless DR detectors can be positioned about the patient in any number of positions, without the concern for mounting hardware or extended wires and cabling between the detector and image acquisition and power electronics. Portability with wireless operation also makes these devices suitable for use in veterinary imaging, since the DR detector can be flexibly positioned and there are no external wires that could be chewed, trampled, or otherwise damaged during handling and positioning about the subject. It is also possible to use the DR detector in various outdoor environments, under a range of weather conditions.

In conventional use as well as in veterinary, outdoor, and industrial and security imaging environments, however, the portable DR detector is continually exposed to surface contamination from microorganisms. A number of mechanisms and practices have been adopted to keep the DR detector free from bio-contaminants, including encasement of the detector in a disposable envelope that is replaced for each patient and regular cleaning of the detector surface with a disinfectant. Even with these techniques faithfully followed, however, there is still an ongoing element of risk for a DR detector that is in constant use. Even where cleaning and packaging procedures for the detector are regularly executed, for example, operator handling between exams or during re-charging can inadvertently introduce microorganisms that could be passed along to the patient or to others who come in contact with the DR detector in normal handling. Even the likelihood of airborne contamination is a concern.

Thus, there is a need for a DR detector housing that provides a high measure of resistance to microorganisms and reduces the likelihood of pathogen attachment and growth.

SUMMARY

Embodiments of the present disclosure are directed to advancing the art of diagnostic x-ray imaging. Particular embodiments described herein can address the need for a DR detector housing that has antimicrobial properties.

These objects are given only by way of illustrative example, and such objects may be exemplary of one or more embodiments of the invention. Other desirable objectives and advantages inherently achieved by the may occur or become apparent to those skilled in the art. The invention is defined by the appended claims.

According to one aspect of the disclosure, there is provided a digital radiography detector including a two dimensional array of photosensors electrically connected to control electronics for capturing and reading out image data captured in the photosensors. A rigid housing encloses the photosensors and the control electronics, and includes surface having antimicrobial material to inhibit growth of pathogens on the surface of the housing.

BRIEF DESCRIPTION OF THE DRAWINGS

The foregoing and other objects, features, and advantages of the invention will be apparent from the following more particular description of the embodiments of the disclosure, as illustrated in the accompanying drawings. The elements of the drawings are not necessarily to scale relative to each other.

DETAILED DESCRIPTION OF THE EMBODIMENTS

Figure 1:
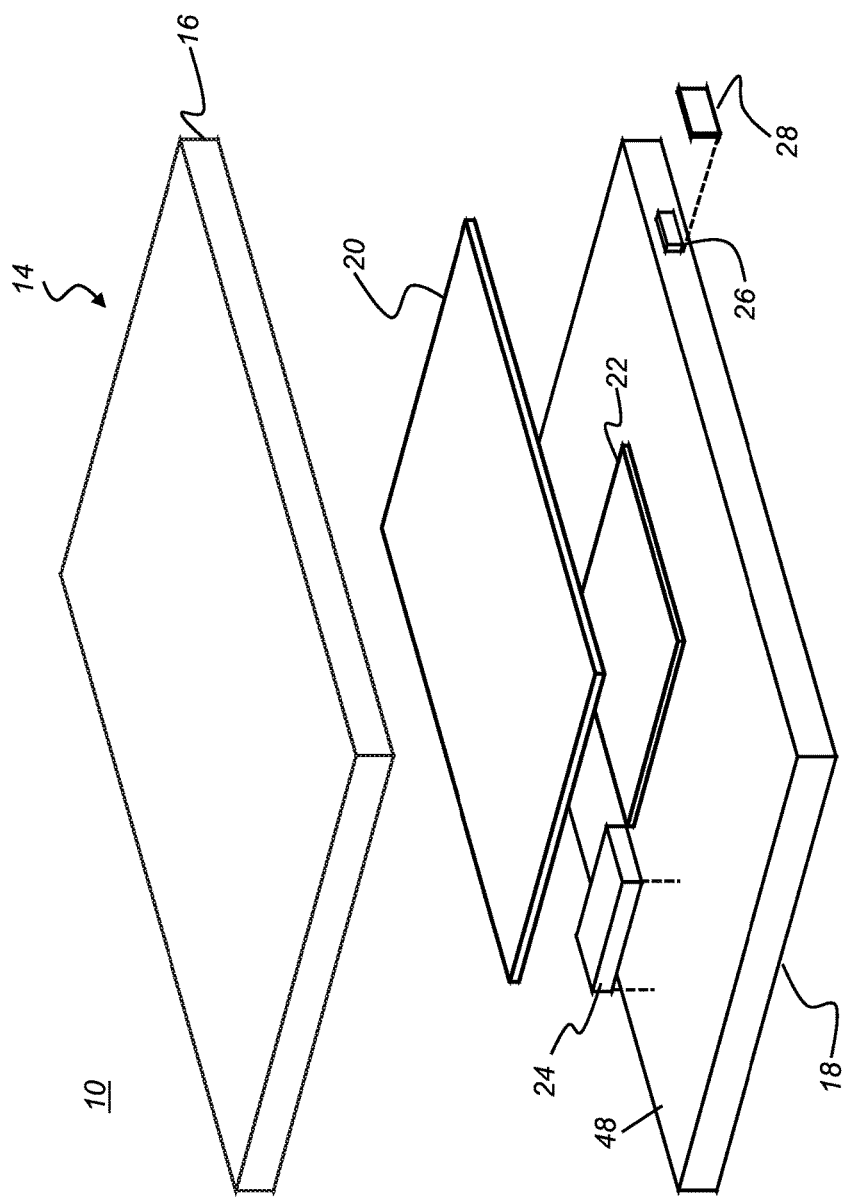
FIG. 1 is an exploded view showing some of the parts of a portable digital radiography (DR) detector.

The following is a detailed description of the preferred embodiments, reference being made to the drawings in which the same reference numerals identify the same elements of structure in each of the several figures.

The exploded view of FIG. 1 shows, in simplified form, some of the electrically active internal components of a DR detector 10 that are protected within a substantially rigid enclosure or housing 14 formed using multiple parts, including top and bottom covers 16 and 18, respectively. A detector core assembly 20 includes a scintillator layer and a two dimensional array of photosensitive elements. The scintillator material outputs light energy upon impact by x-rays and the array generates image data according to an amount of the light energy that each photosensitive element receives. A circuit board 22, in signal communication with detector core assembly 20, provides control electronics for reading out the image data from the array and for image processing. The circuit board 22 may include wireless transmission capability for transmitting image data to an external host processing system. A battery 24 provides power, acting as a voltage source for detector 10 operations. A port 26 extending through bottom cover 18 is provided to allow electrical connection for receiving and transmitting data, and/or receiving power such as from a voltage supply. The port 26 may have an optional cover plate or sealing cap 28, which may be a rubber seal or other liquid proof material. In addition to the illustrated components, a number of interconnecting cables, supporting fasteners, cushioning materials, connectors, and other elements may be used for packaging and protecting the DR detector circuitry. An optional antenna and/or transmitter, exterior to the control electronics of the circuit board 22 and in signal communication therewith, may be included for wireless communication and may alternately be provided within or as part of the housing 14. Top and bottom housing covers 16 and 18 may be fastened together along a mating surface 48.

Figure 2:
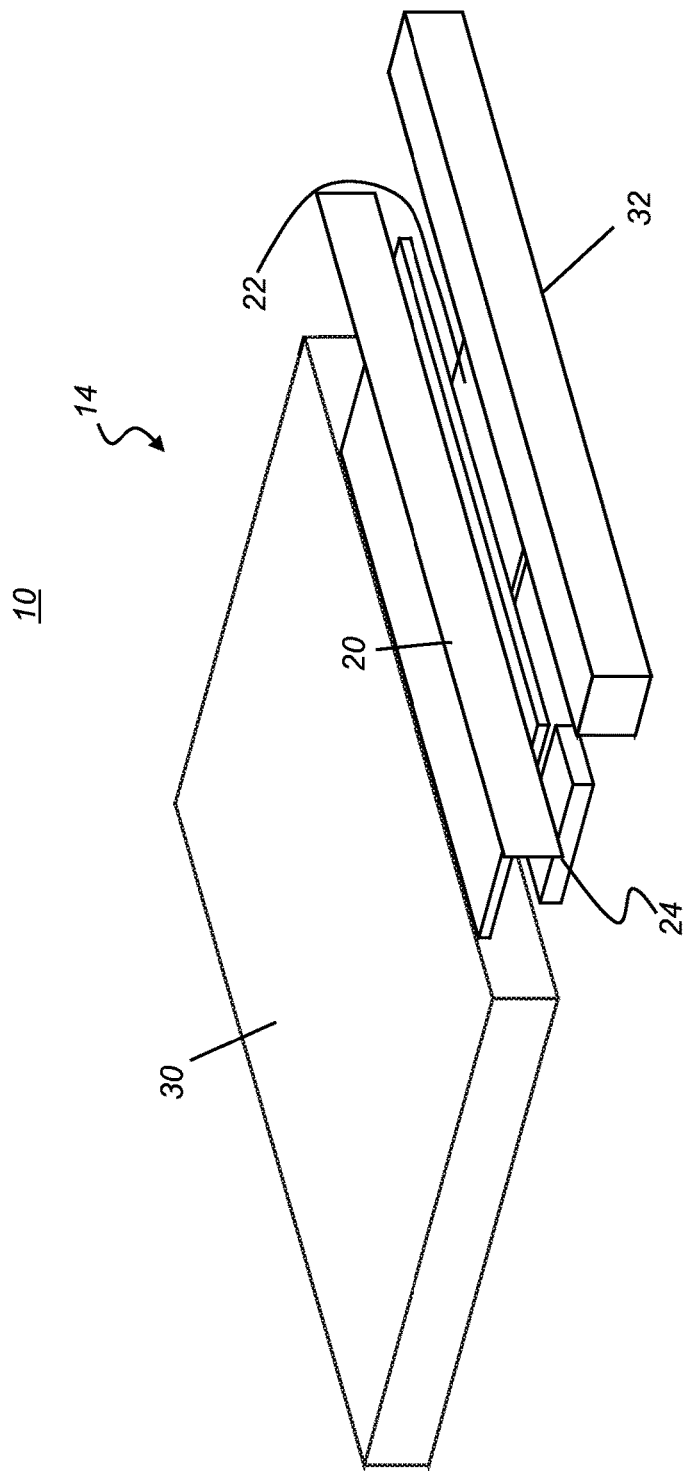
FIG. 2 is an exploded view showing some of the parts of a portable digital radiography (DR) detector according to an alternate embodiment.

The exploded view of FIG. 2 shows an alternate embodiment of DR detector 10, in which detector core assembly 20, circuit board 22, and battery 24, along with interconnection and other support components, slide into a cover 30. A lid 32 then fastens to cover 30 and provides a protective seal.

Protection from pathogens or microorganisms is a concern for either of the FIG. 1 or FIG. 2 DR detector configurations, or for any portable DR detector configuration. This concern relates not only to broad external surfaces of the DR detector 10, but also to areas surrounding and within cover plates, plugs, connectors, and other interfaces. An embodiment of the present disclosure addresses the need for providing a housing that has inherent antimicrobial properties and has features or composition that inhibit the presence or growth of pathogens on various surfaces and components of the detector.

According to an embodiment of the present disclosure, the materials used for conditioning housing 14 to inhibit growth of pathogens can be antimicrobial by virtue of surface features of the housing, materials used to manufacture the housing, coatings or treatments applied to the housing, or other physical features of the housing. Antimicrobial conditioning of the detector housing 14 may serve to inhibit pathogen habitation on internal as well as external surfaces and components.

Housing Surface with a Micro-Pattern

Figure 3:
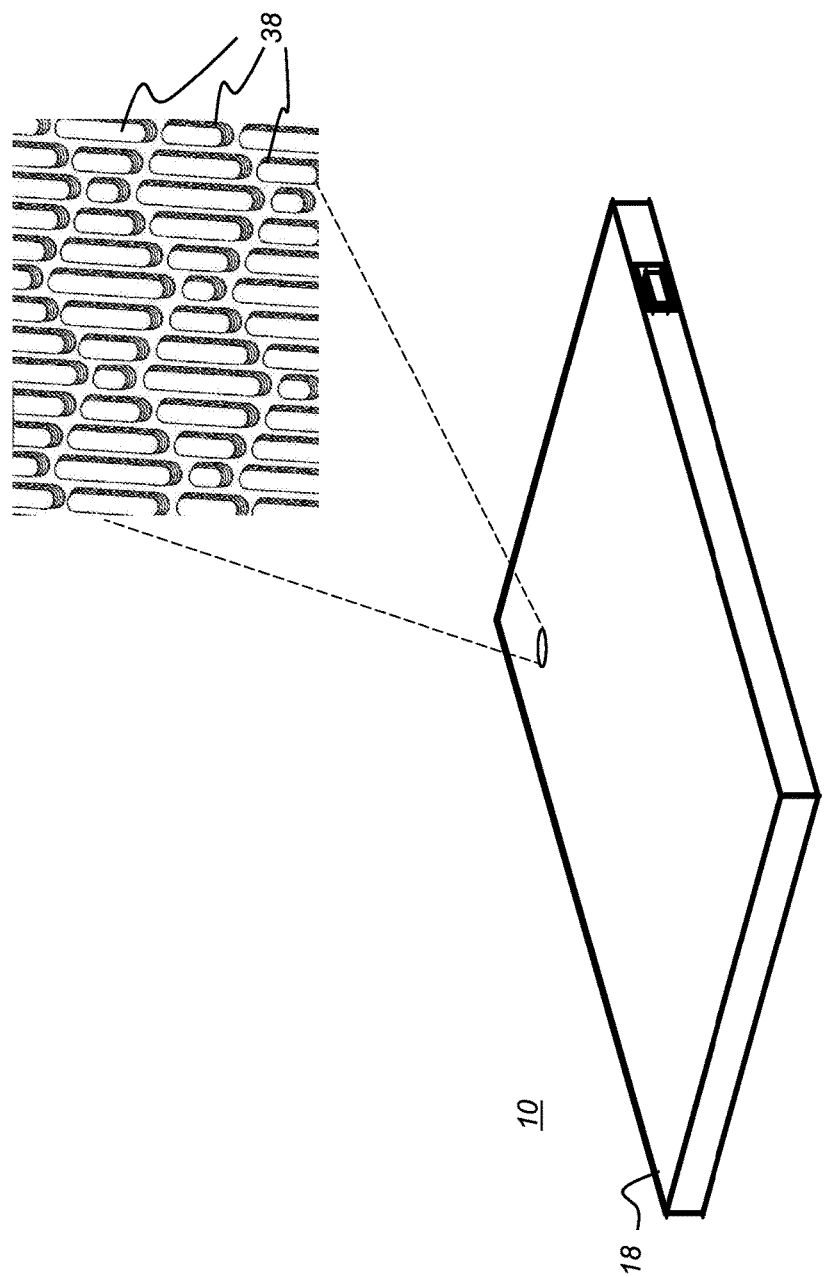
FIG. 3 is a perspective view showing a DR detector with a featured surface having a micropattern.

According to one embodiment as shown in FIG. 3, a pattern of spaced apart micro-features 38 is formed on a portion of the housing surface including a portion of cover 18 of the detector 10. The patterned surface topography is designed to resist bioadhesion, a behavior in which bacteria or other unicellular microorganisms find suitable conditions along a surface that allow their habitation thereon via nourishment, growth, and reproduction. By imparting a patterned topography onto a surface of the cover 18, this configuration defeats or substantially reduces bioadhesion, forming a surface that does not support microorganism settling and growth.

Micro-patterning to resist bioadhesion, or biofouling, is described, for example, in U.S. Pat. No. 9,016,221 to Brennan et al., which is hereby incorporated by reference as if fully set forth herein in its entirety. This reference presents a number of guidelines as to micro-pattern sizing, spacing, and aspect ratio for an antimicrobial micro-pattern.

The micro-featured pattern can be molded into one or more housing surfaces during manufacture or can be applied as a layer, as a pattern printed on the cover, or as an adhesive coating, for example. The micro-pattern may also be etched into the housing surface, such as by using laser etching.

Employing Antimicrobial Materials

Alternately, the detector 10 housing can be formed from materials that have antimicrobial properties, including toxicity to pathogens. The use of silver and its compounds such as silver salts, for example, is known for its antibacterial properties and for reducing biofilm activity. Silver ions and silver nanoparticles (AgNPs) are used in hydrogels for wound treatment, for example. Metallic silver, silver oxides, and silver salts are highly effective antimicrobials which control infection by killing bacteria and viruses at wound sites, for example. Silver ions appear to block infection by forming insoluble compounds within the cell walls, blocking respiratory chains, and binding and denaturing bacterial DNA, thereby preventing replication. Silver ions tend to disrupt microbial cell walls and can also damage cell receptors by binding metabolically ineffective compounds to cell metabolic pathways.

Silver-based biocides have also shown activity against decay fungi, some common molds and some insects. Ionic silver is recognized as an effective bactericide at levels of about 0.1 μg/L, while fungicidal activity may require higher levels. To maintain effectiveness against bacterial growth, silver ions must be released continuously at effective levels in order to compensate for decrease in effective concentration due to these binding interactions. Silver exhibits antimicrobial activity against many pathogens; silver based coatings have been proposed for use on surfaces of implanted medical devices of various types to help reduce the risk of serious infection from such in vivo devices. Applications of silver and silver oxide coatings have included hydrogels imbedded with silver compounds, wet chemistry using silver salts and antimicrobial compounds, and plasma vapor deposited surfaces of silver, cast silver, and cryogenically applied silver.

Materials used to condition the housing of the DR detector for antimicrobial properties can include any of silver, copper, zinc, or other metals and their salts or other compounds, organosilanes, a resin, fluorocarbons, Gallium, Titanium Dioxide, or other material with suitable pathogen-inhibiting characteristics. Superhydrophic materials, resilient to liquid presence or penetration, can also be used as antimicrobial materials for device interfaces.

U.S. Pat. No. 7,041,723 to Kimura describes a resin having antimicrobial properties, which patent is hereby incorporated by reference as if fully set forth herein in its entirety.

The housing may be molded from an antimicrobial material or may have such a material additive combined with or infused into one or more of its surfaces. The antimicrobial material can alternately be coated onto the housing and, after some time, recoated onto the housing to thereby condition and recondition the housing surfaces with one or more added layers of material that inhibits pathogenic growth or that is toxic to bacteria and other pathogens.

Coating processes that can be used for silver-containing materials or other materials suitable for antimicrobial characteristics can include sputtering, ion beam assisted deposition (IBAD), and dip processes. Coating may be applied in a pattern, as described previously with reference to FIG. 3.

Using Light-Activated Antimicrobials

A number of antimicrobial materials can be light-activated. These materials may use any of various types of photosynthesizers including various types of naturally occurring compounds (such as porphyrins and anthraquinones), dyes (such as methylene blue, toluidine blue), or various cyanine compounds, and materials having added gold nanoparticles. Materials containing photocatalyst nanoparticles can alternately be used for providing resistance to pathogens. Nanoparticles of the oxides of silver, zinc and copper can be used, for example.

Methods for incorporating light-activated antimicrobial materials into the housing surface can include bonding or diffusion, as described by researchers Noimark, Parkin, and Allan in an article entitled "Scientists Develop World's First Light-Activated Antimicrobial Surface that Also Works in the Dark" in *Med Device Online*, Mar. 24, 2014, for example.

U.S. Patent Application No. 2001/0047195 by Crossley describes the use of light-activated chemical substances that can be used as antimicrobials, which is hereby incorporated by reference as if fully set forth herein in its entirety. The applied light can be in the range between about 200 and about 1400 nm.

U.S. Pat. No. 9,125,973 to Bui et al. describes an antimicrobial housing using light-activated dyes, which is hereby incorporated by reference as if fully set forth herein in its entirety.

U.S. Pat. No. 8,623,446 to McGrath et al. describes the use of antimicrobial surfaces whose toxicity to pathogens is activated by ultraviolet (UV) or near-ultraviolet light, which is hereby incorporated by reference as if fully set forth herein in its entirety.

U.S. Patent Application No. 2006/0188389 entitled "Method and system for reducing microbes on a portable electronic device" by Levy shows a system that irradiates a cell phone or other portable device during charging, which is hereby incorporated by reference as if fully set forth herein in its entirety.

This application is related in certain respects to U.S. patent application Ser. No. 14/308,981, filed Jun. 19, 2014, in the name of MacLaughlin et al., and entitled LIQUID RESISTANT DIGITAL DETECTOR, describing hydrophobic materials, which is hereby incorporated by reference as if fully set forth herein in its entirety.

Figure 4:
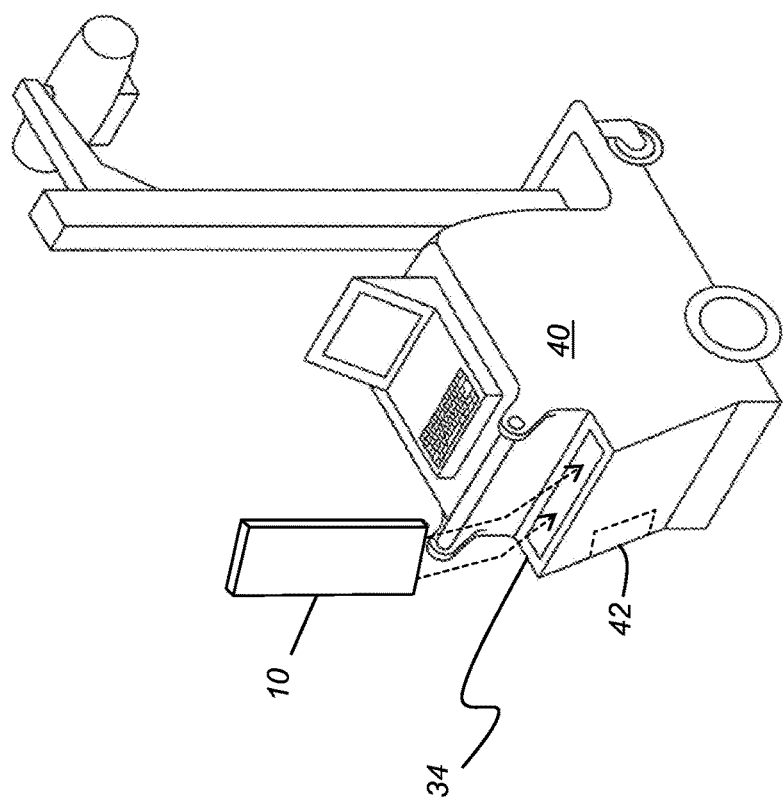
FIG. 4 is a perspective view showing a mobile radiographic imaging system using a portable digital radiography detector.

The perspective view of FIG. 4 illustrates a mobile radiography imaging system cart 40 used for portable radiographic imaging which may include a light chamber, or slot, 34 that is used to disinfect DR detector 10 which may be placed in the chamber 34 such as while the cart 40 is in transit between examinations. The light source assembly 42 that is used within light chamber 34 may include one or more UV light sources, such as a UV lamp, or other light source emitting an appropriate wavelength range for activating antimicrobial material on housing surfaces of the detector 10. The irradiation from a UV light source may include UV-A, UV-B, or UV-C light, such as from light-emitting diodes (LEDs) or from an electroluminescent (EL) device.

According to an embodiment of the present disclosure, a UV light source assembly 42 used to irradiate light chamber 34 may be energized automatically when DR detector 10 is inserted into the chamber 34, such as by having a sensor in the light chamber 34 transmitting a signal to the light source assembly 42 when a detector insertion is sensed. Irradiation by the light source may be continuous or pulsed. An internal light source s\assembly 42 for chamber 34 can include a coherent light source, such as a scanning laser or line laser. The internal light source assembly 42 for chamber 34 may include an array of emissive sources disposed to direct light onto detector 10 from different angles. A supplementary disinfectant can also be applied to detector 10 housing surfaces, such as when the detector 10 is inserted or removed.

Combined Featuring and Materials Solutions

An alternate embodiment combines an antimicrobial material, such as an applied coating, with a patterned DR detector surface to condition it with a toxicity that is harmful to bacteria and other pathogens. Surface patterns described with reference to the example of FIG. 3 may increase the surface area of an antimicrobial material, effectively increasing its antimicrobial activity. For example, ion beams can be used to carve textures into surfaces, as is performed on various types of human body implantable devices, hydrocephalic shunts, percutaneous connectors, and orthopedic prostheses. The patterns used for some of these textures may include holes, columns, cones, or pyramids, each as small as one micron. These added patterns increase a device's surface area by as much as 20 times or more and therefore increase antimicrobial activity of deposited coatings, as described in U.S. Pat. No. 5,383,934, which is incorporated by reference as if fully set forth herein in its entirety. 3-D printing can be used to form the detector housing having a suitable antimicrobial micro-pattern or formed from an antimicrobial material.

The invention has been described in detail, and may have been described with particular reference to a suitable or presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A radiography apparatus comprising:
   electronic circuits; and
   a substantially rigid housing enclosing the electronic circuits,
   wherein the housing comprises antimicrobial material to inhibit growth of pathogens on a surface of the housing, and
   wherein the antimicrobial material comprises an antimicrobial property that is activated by exposure to light.

2. The apparatus of claim 1, further comprising a digital radiography detector having a two dimensional array of photo sensors,
   wherein the electronic circuits comprise control electronics electrically connected to the photosensors, and
   wherein the housing comprises a substantially rigid housing enclosing the photosensors and the control electronics.

3. The apparatus of claim 2, wherein the surface of the housing is an exterior surface of the housing.

4. The apparatus of claim 1, wherein the material is selected from the group consisting of silver, copper, organosilanes, a resin, fluorocarbons, Gallium, Titanium Dioxide, and a superhydrophobic material.

5. The apparatus of claim 1, wherein the material comprises a coating.

6. The apparatus of claim 1, wherein the housing further comprises a material having a micro pattern formed therein.

7. The apparatus of claim 1, wherein the light comprises light having an ultraviolet wavelength.

8. The apparatus of claim 1, wherein the antimicrobial material comprises photocatalyst nanoparticles.

9. The apparatus of claim 1, wherein the antimicrobial material is plasma vapor deposited.

10. A method of fabricating a digital radiography detector, the method comprising:
    providing a core assembly having a scintillator and a two dimensional array of photosensors;
    providing control electronics electrically connected to the photosensors;
    forming a substantially rigid housing configured to enclose the core assembly and the control electronics; and
    imparting an antimicrobial property onto the housing, including
    implanting an antimicrobial material into the housing.

11. The method of claim 10, further comprising patterning an antimicrobial texture on the antimicrobial layer.

12. The method of claim 10, further comprising applying an antimicrobial material on the antimicrobial texture.

13. The method of claim 10, further comprising coating the housing with an antimicrobial material.

14. A mobile digital radiography system comprising:
   a portable digital radiography detector comprising:
      a two dimensional array of photosensors;
      control electronics electrically connected to the photosensors; and
      a substantially rigid housing enclosing the photosensors and the control electronics, a surface of the housing comprising a light-activated antimicrobial material to inhibit growth of pathogens; and
   a mobile cart comprising:
      an x-ray source; and
      a light chamber sized to hold the digital radiography detector, the light chamber having a light source energizable to direct light onto the housing surface to enhance antimicrobial effectiveness of the light-activated antimicrobial material.

15. The system of claim 14, wherein the light source is an ultraviolet light source.

16. The system of claim 14, wherein the light source comprises an array of light emitting diodes.

* * * * *